US006309410B1

(12) United States Patent
Kuzma et al.

(10) Patent No.: US 6,309,410 B1
(45) Date of Patent: Oct. 30, 2001

(54) COCHLEAR ELECTRODE WITH DRUG DELIVERY CHANNEL AND METHOD OF MAKING SAME

(75) Inventors: Janusz A. Kuzma, Englewood, CO (US); Thomas H. R. Lenarz; Rolf-Dieter Battmer, both of Hannover (DE); Alfred E. Mann, Hollywood, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/375,425

(22) Filed: Aug. 17, 1999

Related U.S. Application Data

(63) Continuation-in-part of application No. 09/140,034, filed on Aug. 26, 1998, now Pat. No. 6,038,484.
(60) Provisional application No. 60/101,942, filed on Sep. 25, 1998, and provisional application No. 60/134,290, filed on May 14, 1999.

(51) Int. Cl.[7] .................................................. A61N 1/05
(52) U.S. Cl. ................................................................ 607/137
(58) Field of Search ............................... 607/120, 137, 607/136, 55, 56, 57

(56) References Cited

U.S. PATENT DOCUMENTS

| | | | |
|---|---|---|---|
| 4,819,647 | 4/1989 | Byers et al. | 128/642 |
| 5,119,832 * | 6/1992 | Xavier | 607/120 |
| 5,545,219 | 8/1996 | Kuzma | 128/642 |
| 5,645,585 | 7/1997 | Kuzma | 623/10 |
| 5,697,951 | 12/1997 | Harpstead et al. | 607/3 |
| 5,833,714 * | 11/1998 | Loeb | 607/137 |
| 5,929,041 | 7/1999 | Magal | 514/44 |
| 6,070,105 * | 5/2000 | Kuzma | 607/137 |

OTHER PUBLICATIONS

Lehner, et al., "A Totally Implantable Drug Delivery System For Local Therapy of the Middle and Inner Ear", 2nd International Symposium on Electric Implants in Otology and Conventional Hearing Aids, Goteborg, Sweeden, (Jun. 1996).

* cited by examiner

Primary Examiner—Scott M. Getzow
(74) Attorney, Agent, or Firm—Bryant R. Gold

(57) ABSTRACT

An electrode array suitable for insertion into the cochlea has a drug delivery channel therein. In a preferred embodiment, electrical stimuli may be applied near the modiolar wall of the cochlea via spaced-apart electrode contacts embedded along a front edge of a flexible carrier, which flexible carrier comprises the body of the electrode array. The front edge, and hence the electrode contacts, may be held against the modiolar wall by a flexible positioner placed on the back side of the flexible carrier. Drugs may be delivered deep into the cochlea through the drug delivery channel that passes longitudinally through the center of the flexible carrier. In an alternative embodiment, the drug delivery channel may be included within the positioner.

22 Claims, 9 Drawing Sheets

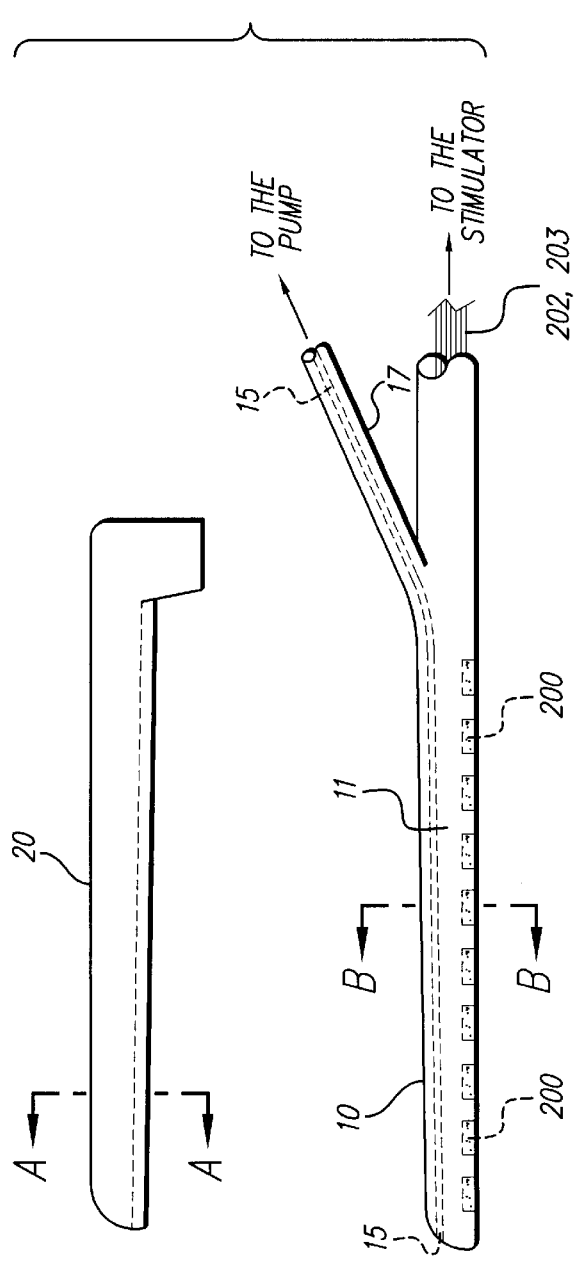
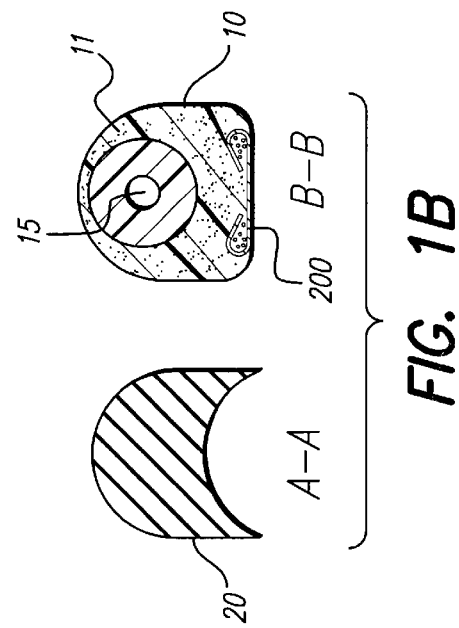
FIG. 1A
FIG. 1B

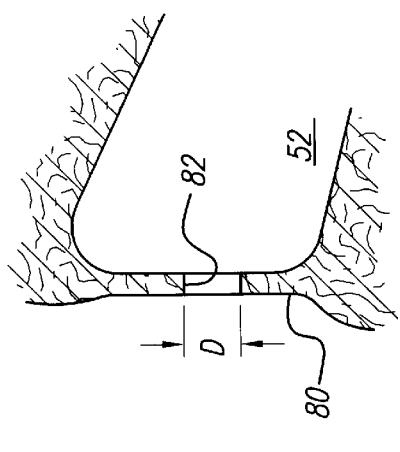
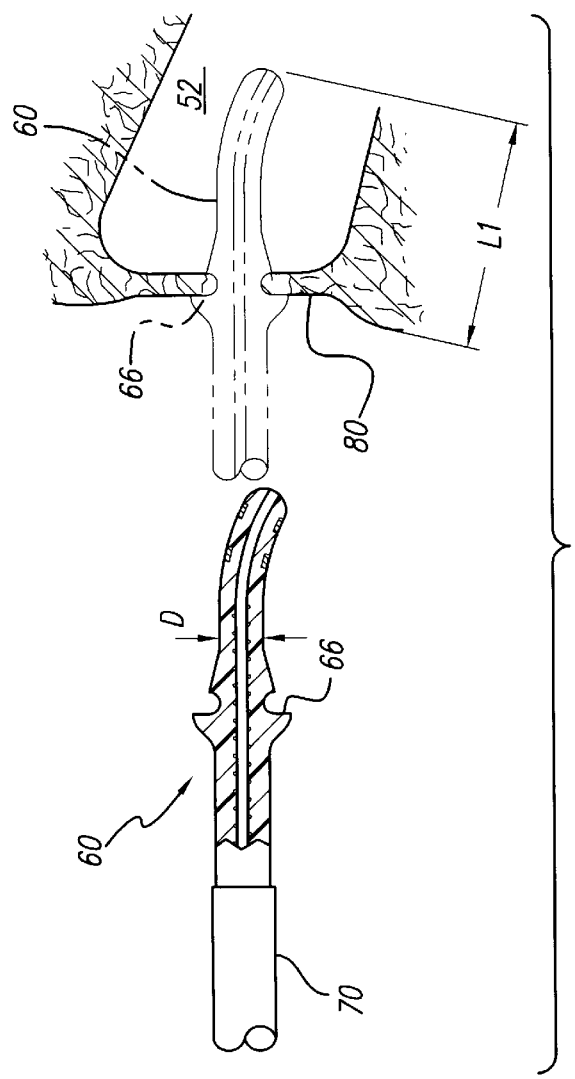
FIG. 9
FIG. 10

COCHLEAR ELECTRODE WITH DRUG DELIVERY CHANNEL AND METHOD OF MAKING SAME

This application is a continuation-in-part (CIP) of U.S. patent application Ser. No. 09/140,034, filed Aug. 26, 1998, now U.S. Pat. No. 6,038,484 which application is incorporated herein by reference; and this application further claims the benefit of the following U.S. provisional patent applications, each of which is also incorporated herein by reference: Ser. No. 60/101,942, filed Sep. 25, 1998; and Ser. No. 60/134,290, filed May 14,1999.

BACKGROUND OF THE INVENTION

The present invention relates to implantable stimulation devices, e.g., cochlear prosthesis used to electrically stimulate the auditory nerve, and more particularly to an electrode array having a drug delivery channel formed therein. Preferably, such electrode array is adapted for use with a cochlear stimulator, and is designed to hug the modiolus so as to place electrode contacts of the electrode array in close proximity to the ganglion cells and thereby to the auditory nerve fibers. The invention also relates to a method of making such an electrode array.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlea (the hair cells are located in the vicinity of the radially outer wall of the cochlea) by presenting electrical stimulation to the auditory nerve fibers directly, leading to the perception of sound in the brain and an at least partial restoration of hearing function. The common denominator in most of these cochlear prosthesis systems has been the implantation into the cochlea of electrodes which are responsive to a suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference. Unfortunately, while the electrode shown in the '647 patent represents a significant advance in the art, there exists lack of sufficient shape memory associated with the electrode to allow it to return to its original curvature (once having been straightened for initial insertion) with sufficient hugging force to allow it to wrap snugly against the modiolus of the cochlea.

It is also known in the art, as shown in applicant's prior patents, U.S. Pat. Nos. 5,545,219 and 5,645,585, to construct an electrode carrier from two initially straight members, a rodlike electrode carrier and a flexible rodlike positioning member. As shown in these patents, the two members extend in substantially parallel relation to and closely alongside each other, but are connected to each other only at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference.

Unfortunately, while the electrode array taught in the above-referenced '219 and '585 patents has the right idea, i.e., to force the electrode carrier into a close hugging engagement with the modiolus, it does so only by use of an additional element that makes manufacture of the lead more difficult and expensive, and only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

Thus, while it has long been known that an enhanced performance of a cochlear implant can be achieved by proper placement of the electrode contacts close to the modiolar wall of the cochlea, two main problems have faced designers in attempting to achieve this goal. First, it is extremely difficult to assemble electrode contacts on the medial side of the an electrode array, facing the modiolus of the cochlea. Second, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes are generally positioned too far way from the modiolar wall.

It is thus evident that improvements are still needed in cochlear electrodes, particularly to facilitate assembling an electrode so that the electrode contacts are on the medial side of the electrode array, and to better assure that the electrode assumes a close hugging relationship with the modiolus once implantation of the electrode has occurred.

It has also been generally known that certain drugs may be used by direct injection into the cochlea to achieve desired therapeutic results, e.g., fibrous tissue prevention, neural growth, tinnitus suppression, and the like. Drug injection into the cochlea may be needed in some patients who are affected by deafness and who are candidates for an electrical stimulator, such as a cochlear implant. Disadvantageously, heretofore there has been no good way to inject drugs into the cochlea of a patient fitted with a cochlear electrode array.

SUMMARY OF THE INVENTION

The present invention addresses the above and other needs by providing an electrode system that allows for both the correct positioning of the electrode contacts against a tissue wall, e.g., the modiolar wall of the cochlea, and which further includes a drug delivery channel through which drugs may be injected directly into the region near the tissue wall being stimulated, e.g., deep into the cochlea.

A preferred electrode with a drug delivery channel in accordance with the invention comprises a cochlear electrode array, adapted for insertion into the scala tympani of the cochlea. Preferably, an electrode positioner is used with the electrode array to press or hold the electrode contacts of the array against the modiolar wall of the cochlea. A drug delivery channel is formed within the body of the electrode array and/or the within the body of the positioner, allowing drugs to be administered through such channel.

More particularly, in accordance with one aspect of the invention, correct positioning of the electrode contacts against the modiolar wall of the cochlea is achieved through the use of an electrode system that includes an electrode array, preferably made in a slightly curved shape, for improved stability of electrode contact direction, made on a flexible carrier so that it can easily bend within the cochlea. The electrode contacts, and the wires that connect with the electrode contacts, are molded into the array along a front edge. A drug delivery channel is formed in the center of the flexible carrier in that portion of the carrier adapted for insertion into the cochlea, with an open end of the channel being located at or near the distal end of the array. A proximal end of the drug delivery channel, accessible at a proximal end of the array, i.e., at that end that still remains outside of the cochlear after the main body of the array has been inserted into the cochlea, may be connected to a drug delivery pump or a hypodermic needle or other drug delivery means.

In a preferred application, the electrode array is inserted into the scala tympani of the cochlea such that the front edge of the array (the edge wherein the electrode contacts are found) is facing the modiolar wall. To position and maintain the electrode contacts against the modiolar wall, a flexible positioner is also inserted into the scala tympani duct, behind the electrode array (i.e., on the side of the electrode array opposite the front edge where the electrode contacts are located). The flexible positioner is typically molded from a silicone polymer so as to make it easy to slide into the cochlea, and made to assume a curved shape to facilitate its insertion into the cochlea.

The drug delivery channel is formed within the center of the flexible carrier of the electrode array using a silicone tube. This is done by first making an electrode assembly as described in applicant Kuzma's earlier U.S. patent application Ser. No. 09/140,034, filed Aug. 26, 1998 now U.S. Pat. No. 6,038,484, incorporated herein by reference. This electrode assembly, which is initially carried on a foil carrier, is then placed within a channel or cavity of a molding die, as is a silicone tube. The ends of the silicone tube are temporarily closed and the die is then filled with a liquid polymer, or other suitable substance, and allowed to cure, thereby forming the flexible carrier of the electrode array.

In an alternative embodiment of the invention, the drug delivery channel may be incorporated into the positioner, rather than into the body of the flexible carrier of the electrode array.

It is thus an object of the present invention to provide an electrode array suitable for insertion into the cochlea having a drug delivery channel therein. Electrical stimuli may be applied near the modiolar wall of the cochlea via spaced-apart electrode contacts embedded along a front edge of a flexible carrier, which flexible carrier comprises the body of the array. The front edge, and hence the electrode contacts, is held against the modiolar wall by a positioner placed on the back side of the flexible carrier. Drugs may be delivered deep into the cochlea through the drug delivery channel that passes longitudinally through the center of the flexible carrier. As required, a pump or syringe may be used to push or pump such drugs through the drug delivery channel.

It is another object of the invention to provide a method of making an electrode array having a drug delivery channel.

It is a further object of the invention to provide a mechanism for delivering drugs deep into a cochlea that is already occupied with an electrode array.

BRIEF DESCRIPTION OF THE DRAWINGS

The above and other aspects, features and advantages of the present invention will be more apparent from the following more particular description thereof, presented in conjunction with the following drawings wherein:

FIG. 1A shows a side view of an electrode array and positioner made in accordance with a first embodiment of the invention;

FIG. 1B shows a sectional view of the positioner taken along the lines A—A of FIG. 1A, and a sectional view of the electrode array taken along the lines B—B of FIG. 1A;

FIGS. 9 and 10 illustrate the manner of inserting the electrode array of FIG. 8 into the cochlea by punching or drilling a hole through the round window membrane and inserting the array into the hole using an insertion tool.

Corresponding reference characters indicate corresponding components throughout the several views of the drawings.

DETAILED DESCRIPTION OF THE INVENTION

Figure 2A:
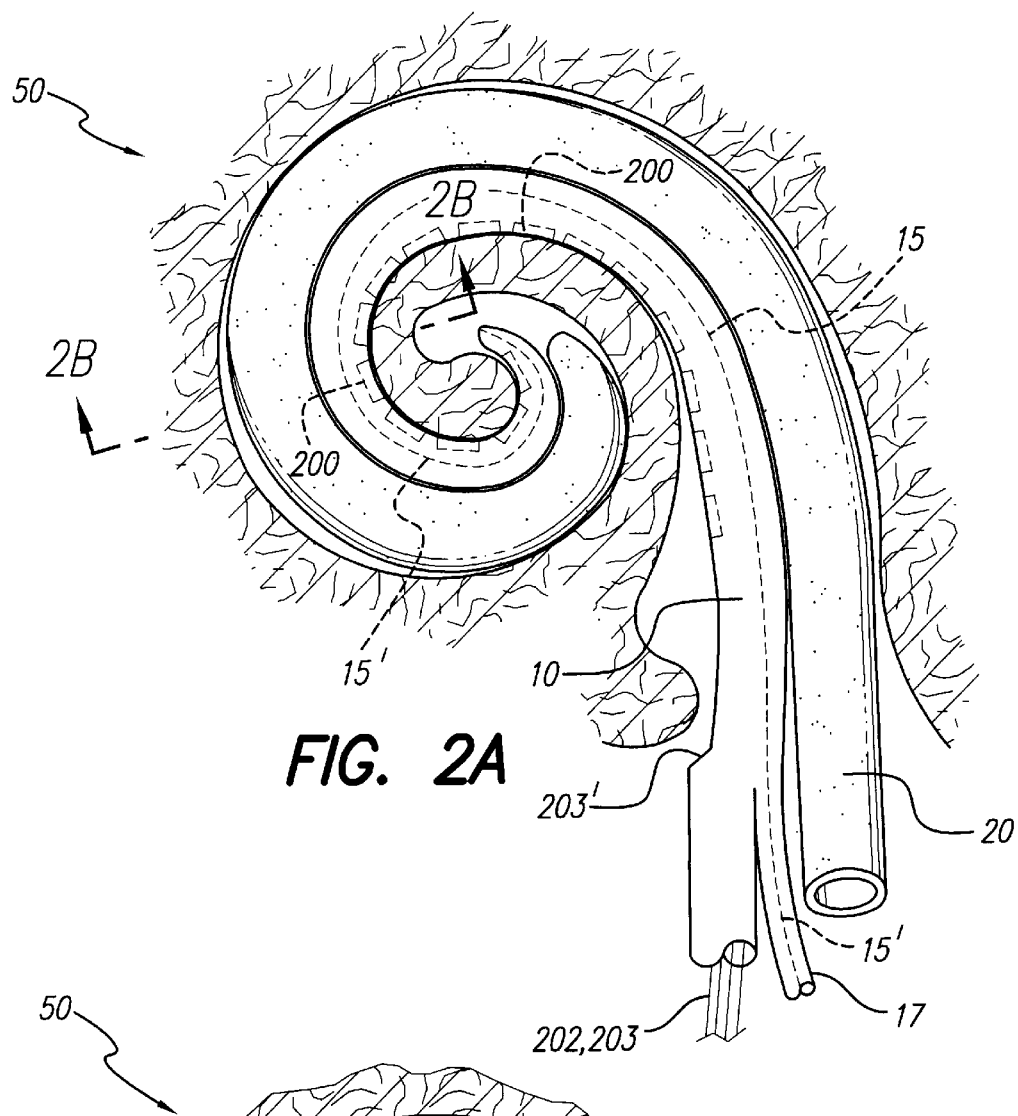
FIG. 2A depicts a side view of the scala tympani of a cochlea, with an electrode array and positioner inserted therein, and also illustrates the path of the drug delivery channel (the dotted line 15') through the electrode array.

The following description is of the best mode presently contemplated for carrying out the invention. This description is not to be taken in a limiting sense, but is made merely for the purpose of describing the general principles of the invention. The scope of the invention should be determined with reference to the claims.

Turning to FIGS. 1A and 1B, there is shown a side and sectional views of an electrode array 10 and a positioner 20 made in accordance with a first embodiment of the invention. The electrode array comprises an elongate flexible carrier 11 into which a plurality of spaced-apart electrode contacts 200 have been embedded. Wires 202, 203, also embedded within the flexible carrier 11, connect each of the electrode contacts to a stimulator (not shown).

A drug delivery channel 15 passes longitudinally through the flexible carrier 11 of the electrode array 10. At a proximal end of the array 10 (note: the proximal end is the end nearest the stimulator) the drug delivery channel branches off of the main body of the flexible carrier 11 to form a drug delivery branch 17 of the array. A proximal end of the branch 17 may be connected to a suitable drug pump, or other device or appliance (e.g., a hypodermic needle), adapted to inject drugs into the channel 15. Drugs injected or pumped into the channel 15 pass through the channel 15 and exit at the distal tip of the array. Small openings or holes may be made along the length of the flexible carrier 11 to access the channel 15, as needed or desired, so that the drug delivered through the channel 15 may also exit the channel at points along the length of the array other than at the distal end.

Figure 2B:
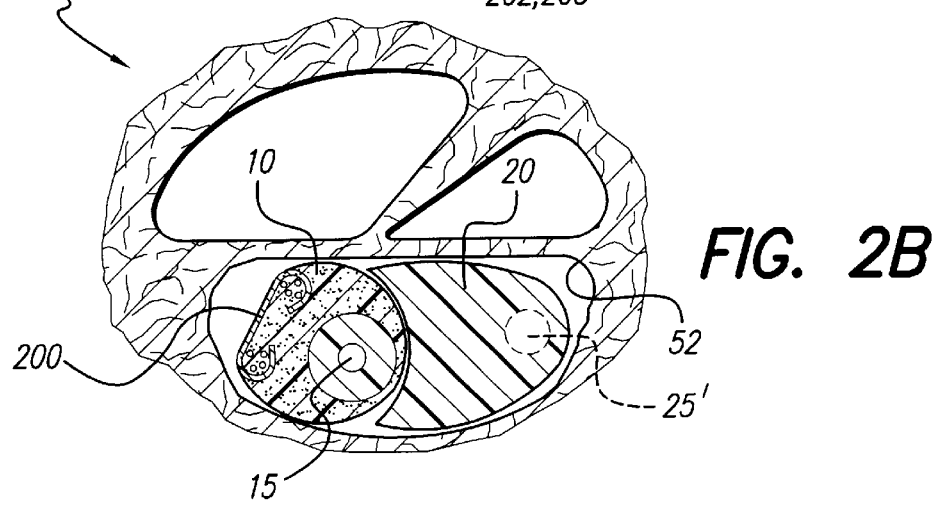
FIG. 2B illustrates a sectional view of the scala tympani of the cochlea of FIG. 2A, taken along the lines A1—A1 of FIG. 2A, and further illustrates how the electrode array fits within a groove or channel along a front edge of the positioner.

As an alternative embodiment, it is noted that the drug delivery channel 15 may also be placed within the positioner 20, as depicted by the channel 25', illustrated with a phantom (dashed) line in FIG. 2B.

As seen in FIG. 2A, it is noted that the electrode array 10 typically includes an offset 203' formed in the flexible carrier 11 near the proximal end. Such offset 203' functions as a stop to prevent the electrode array 10 from being inserted too deep into the cochlea. Even when such offset does not effectively function as a stop, it may always function as a mark, to aid the physician to know when the desired insertion depth has been achieved.

Turning next to FIGS. 3A through 7, a preferred method of making the electrode array 10 will be described. It is to be emphasized that this method of making the electrode array is not the only way an electrode array 10 suitable for use with the electrode system of the invention could be made. Rather, it merely represents an easy and inexpensive (and thus a preferred) way in which the electrode array may be fashioned.

Most designs of electrodes and connectors are based on the principle of molding a contact or array of contacts, usually made from biocompatible metal, into a polymer carrier like silicone or polyurethane rubber. The electrode contacts are usually required to be located in a controlled position in reference to the surface of the carrier, with specified surface areas to be fully exposed to the stimulated or interconnection area. Disadvantageously, making such electrodes or connectors becomes extremely difficult, especially when the contacts are very small and/or a large number of contacts are required, e.g., as is the case with a cochlear electrode. The main problem encountered in the fabrication of such electrodes or connectors is to find a reliable method of holding the system of contacts in the desired and stable position during the process of welding the connecting wires and molding the polymer carrier. A further problem relates to maintaining a controlled surface of the contacts that are to remain exposed, i.e., to ensure that the contacts are not covered by the polymer when the carrier is molded.

The preferred methods of making the electrode array described below in connection with FIG. 3A through FIG. 7 is based on the principle of attaching (by the process of resistance welding) electrode contacts made from precious, biocompatible material (such as platinum or its alloys) to a foil carrier 100 made from a non-toxic but chemically-active metal like iron (Fe). Attached to the metal carrier, the electrode contacts remain in a desired and stable position allowing easy connecting of the wiring system and subsequent molding of the polymer carrier. After completion of the molding process, the metal foil carrier is etched away using a mixture of diluted acids, such as $HNO_3$ and HCl. The precious metal contacts and polymer are immune to the acid and remain in their intact, unaltered shape, and thereby provide the desired electrode array structure.

Figure 3A:
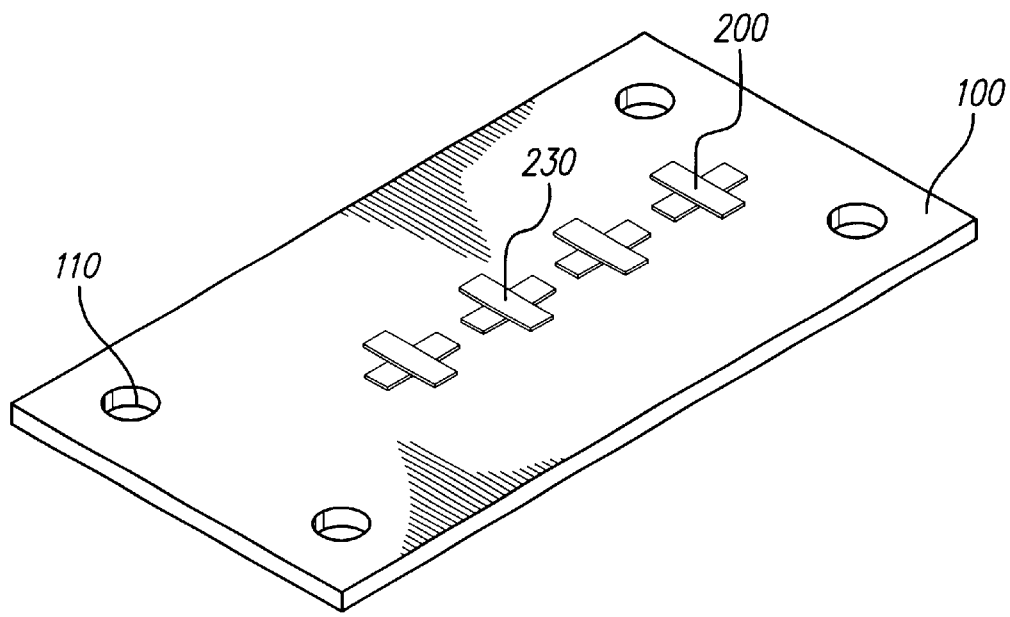
FIG. 3A depicts a preferred manner of making a multi-electrode electrode array of the type shown in FIG. 1A.
Figure 3B:
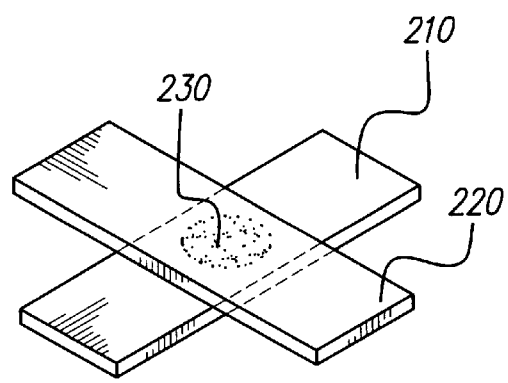
FIG. 3B shows an enlarged view of the electrode contacts of the array of FIG. 1A before such contacts are molded within a flexible carrier body.

To illustrate this method, the method will be described relative to the fabrication of a multi-electrode electrode array 10 of the type shown in FIG. 1A. As a first step, an array of contacts 200 are welded onto an iron carrier 100 so as to assume a desired spaced-apart relationship, as shown in FIG. 3A. Each contact 200 consists of two pieces of platinum foil 210 and 220, connected together and joined to the carrier 100 by a weld 230, as shown in FIG. 3B.

Figure 4A:
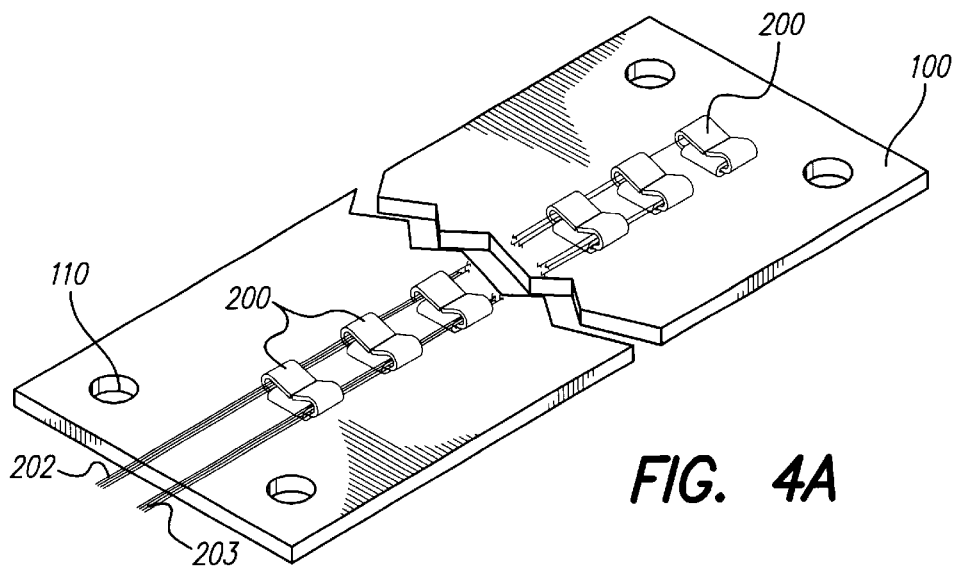
FIGS. 4A, 4B, 4C and 4D illustrate one manner in which wires may be bonded to each of the electrode contacts of FIG. 3B during manufacture of the electrode array.
Figure 4B:
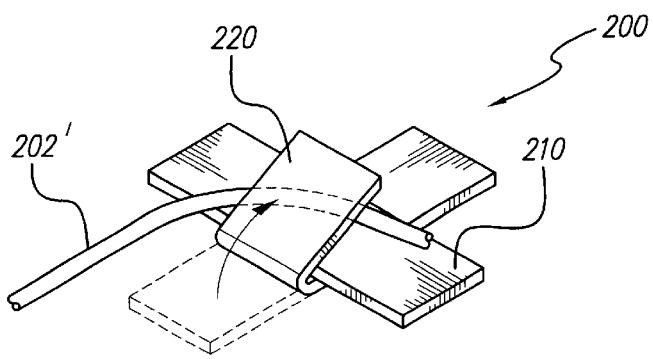
Figure 4D:
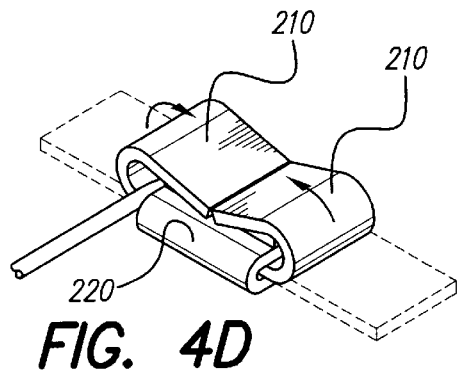
Figure 4C:
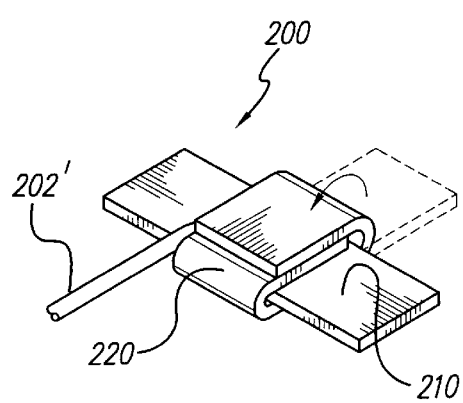

As a second step, a wiring system is connected to each of the electrode contacts 200. This is accomplished as shown in FIGS. 4A, 4B, 4C and 4D. As seen in FIG. 4B, for example, an insulated wire 202', having the insulation removed from its tip, is laid on top of the electrode foil pieces 210 and 220. One of the ends of the foil piece 220 is then folded over to hold the end of the wire while the wire is welded or crimped in position (FIG. 4B). Then, the other end of the foil 220 is folded over the first folded end (FIG. 4C). If other wires are present, e.g., going to electrode contacts further up the array, then such wires may pass over the foil piece 210, lying parallel to the wire 202' so as to form a bundle of wires 202. A similar wire bundle 203 may be formed on the other side of the folded foil piece 220. The ends of the foil piece 210 may then be folded over the folded piece 220 (FIG. 4D) to complete the wire system connection process.

Figure 5:
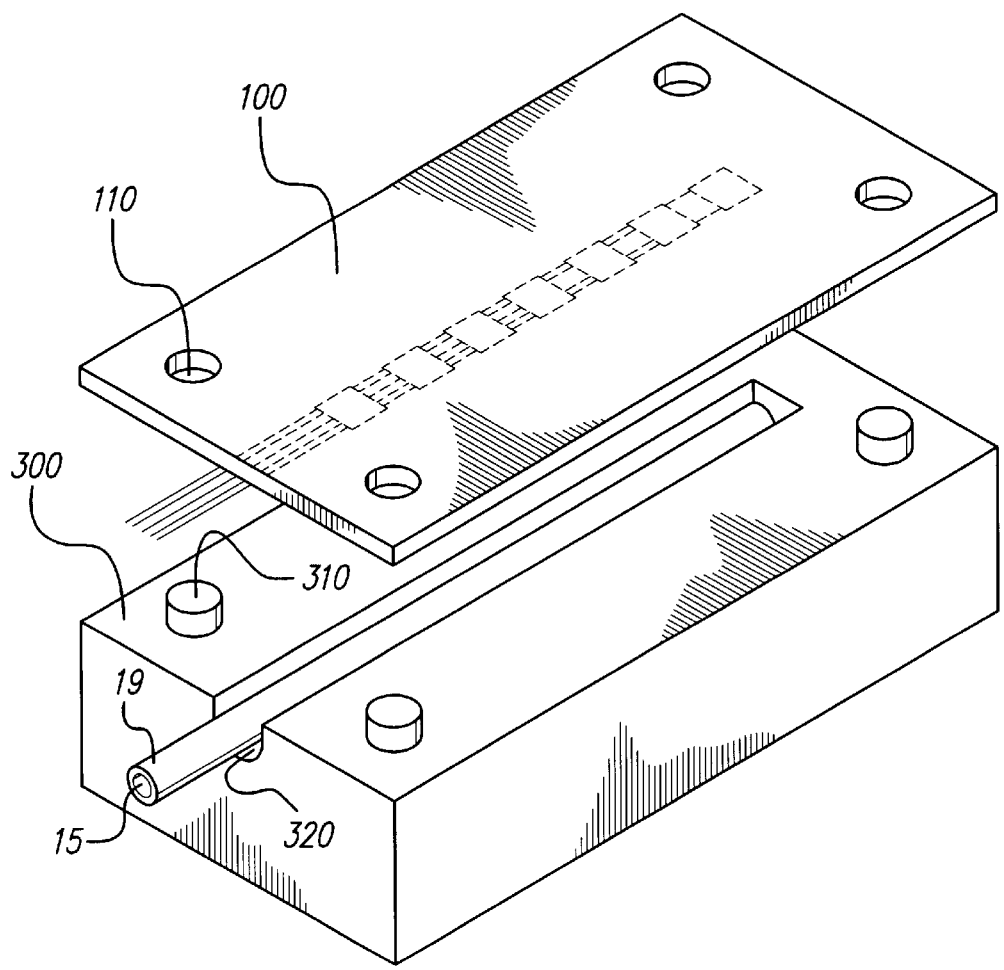
FIG. 5 depicts a molding die onto which the partially-formed electrode array of FIG. 3A, with wires attached to each of the electrodes as shown in FIGS. 4A–4D, may be mounted in order to form a polymer flexible carrier for the electrode array.

Once the wire bundles 202 and 203 have been connected to the electrodes 200, the foil carrier 100 is placed on a molding die 300 as shown in FIG. 5. The die 300 has alignment pegs 310 adapted to align with corresponding alignment holes 110 in the foil carrier 100. The die 300 further has a cavity or channel 320 formed therein into which a silicone tube 19, having a lumen or channel 15 passing therethrough, is placed and held in position, as seen best in the sectional view of FIG. 7. A required amount of material to form the polymer flexible carrier 11 (FIG. 1A) is injected into the die cavity. A distal end of the tube 19 may be temporarily plugged during the molding process to prevent the molding material from clogging the lumen or channel 15 that passes through the tube. The cavity or channel 320 may be shaped or formed as desired.

A similar, but alternate, method of making the electrode array of the present invention is disclosed in U.S. patent application Ser. No. 09/259,199, filed Mar. 01, 1999, now U.S. Pat. No. 6,119,044, which patent is incorporated herein by reference. The alternate method disclosed in the referenced patent application is essentially the same as that shown in FIGS. 3A–4D, except that instead of forming each electrode contact from first and second metallic strips that are formed in an "X" shape, as suggested by FIG. 3B, the first and second metallic strips are formed in a "T" shape. Then, to attach the wiring system, a leg of the "T" is folded back over itself to hold at least one wire of the wiring system therebetween, and the wire and folded "T" leg are electrically bonded together. Then, the sides of the top of the "T" are folded upwardly so that they extend into the flexible polymer carrier, once the flexible polymer carrier is molded over the electrodes and wiring system. When the sides of the "T" are folded up, and when viewed in cross-section through the electrode carrier, they form a "U" shape, as seen, e.g., in FIG. 5A of the referenced patent application, with the silastic tube 19 being positioned within the "U".

Figure 6A:
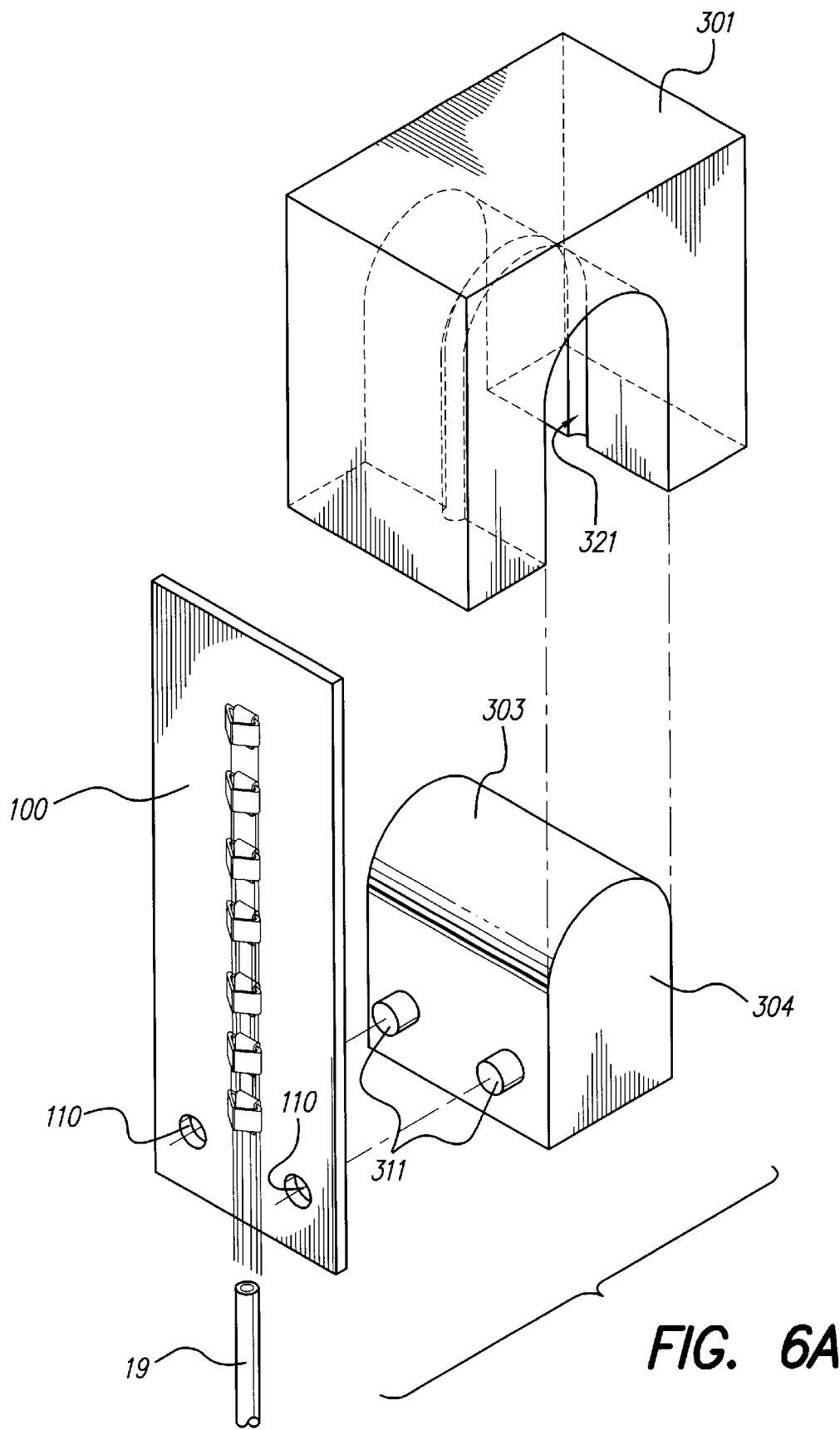
FIGS. 6A and 6B illustrate an alternative type of molding die onto which the partially-formed electrode array of FIG. 3A, with wires attached to each of the electrodes as shown in FIGS. 4A–4D, may be mounted in order to form a polymer carrier for the electrode array.
Figure 6B:
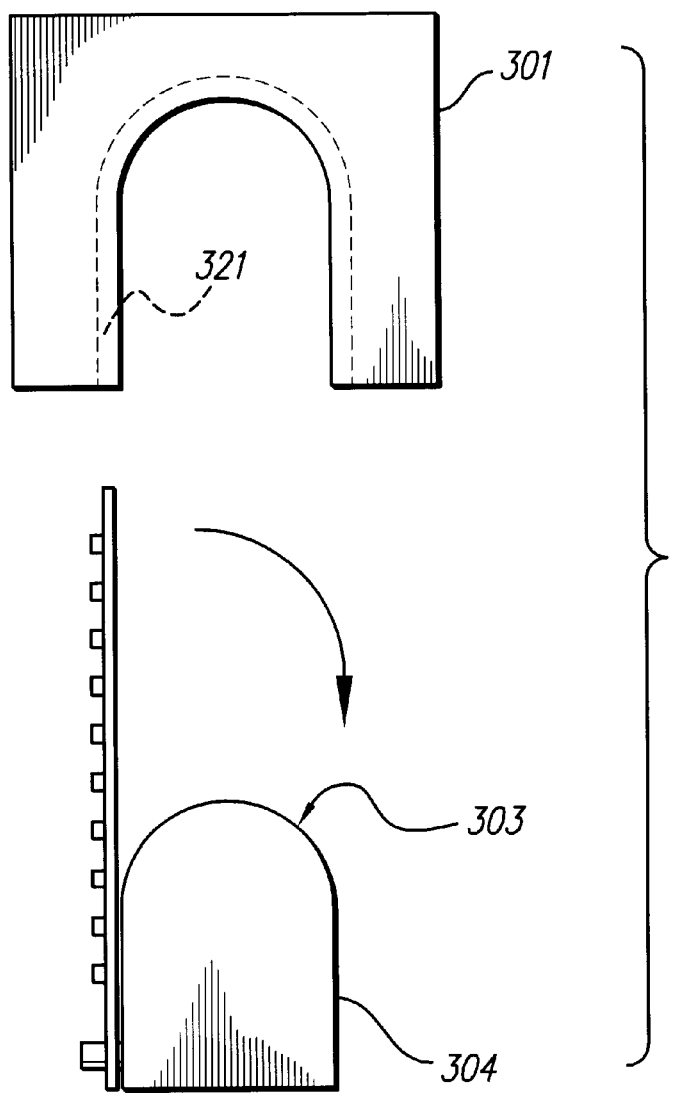
Figure 7:
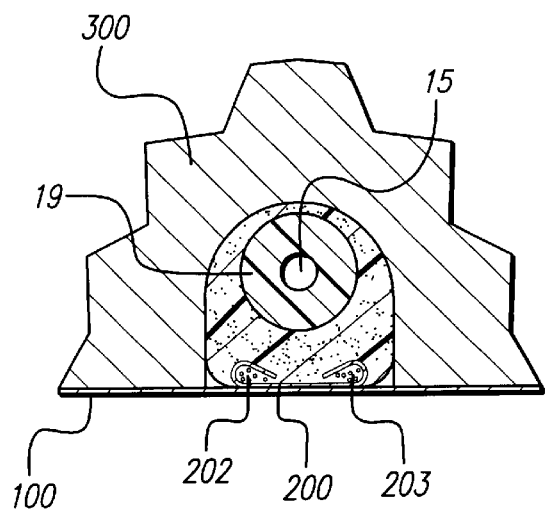
FIG. 7 is a sectional view that illustrates the manner in which the drug delivery channel is formed within the electrode array using a silicone tube placed within the molding die used to form the flexible carrier of the electrode array.

As an alternative to the flat-surface die 300 shown in FIG. 5, a curved die 301 may also be used as shown in FIGS. 6A and 6B. Such die 301 includes a curved surface 303 on a holding block 304 on which the foil carrier 100 may be placed. The block 304 has alignment pegs 311 adapted to align with corresponding alignment holes 110 in the foil carrier 100. The foil carrier 100 is placed on the block 304 and bent over the curved surface 303. The die 301 is then placed over the block 304, with the foil carrier 100 sandwiched therebetween. A channel or cavity 321 is formed in the die 301 having the desired shape and characteristics of the carrier that is to be formed through the molding process. The required amount of material to form the polymer carrier 11, e.g., LSR-70, is then injected into the channel and allowed to cure. By placing the foil carrier assembly 100 in the curved die of FIGS. 6A and 6B (note that FIG. 6A comprises a perspective view of the die 301 and block 304, and FIG. 6B comprises a side or profile view of the die 301 and block 304), the array can be molded or formed to assume the desired curved shape. Such curved shape is preferred to achieve directional stability of the array during insertion.

Thus, it is seen that through proper use of the die 300 or 301/304, or other dies, the electrode array may be formed to assume a natural curved shape, a slightly curved shape, or to be straight.

After the polymer material injected into the die cures, the foil carrier with the electrode array assembly (which is now molded inside of the polymer) is removed from the die 300 or 301 and placed in a mixture of diluted acids. The mixture of diluted acids dissolves the foil carrier 100, thereby exposing a clean surface of the electrode contacts 200. After washing to remove any residue of acids and Fe salts, the main electrode array structure is completed.

Figure 8:
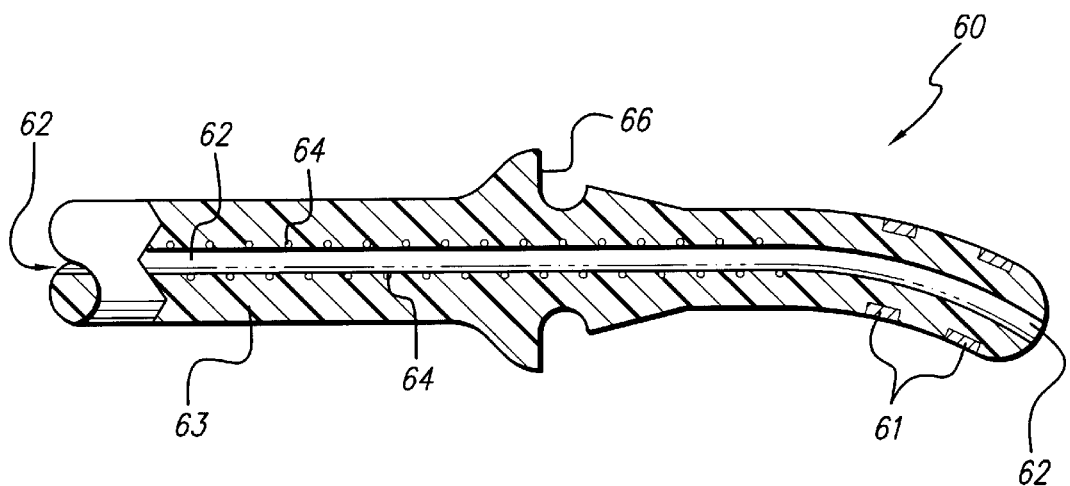
FIG. 8 illustrates a side view of an alternative embodiment of the invention.

Turning next to FIG. 8, a side sectional view of an alternative embodiment of an electrode array 60 made in accordance with the invention is illustrated. Such electrode configuration is especially suitable to those patients with high frequency hearing losses or hearing loss and tinnitus. As seen in FIG. 8, the electrode array 60 has a drug delivery channel 62 therein through which a desired drug may be injected into the same region as is the electrode array. The electrode array 60 comprises a short, e.g., 3–6 mm, thin electrode equipped with one or several electrode contacts 61. The electrode contacts 61 may comprise a ring or a band electrode made from a suitable biocompatible material, such as platinum, that encircles the flexible carrier on which the contacts are carried. Alternatively, the electrode contacts may comprise flat electrode contacts on a modiolar side of the electrode array, as previously disclosed. Each band electrode contact 61 is electrically connected to an insulated coiled lead 64 that is embedded within a flexible polymer body 63. Formed within the flexible body 63 is a retaining collar 66 having an engaging diameter "D". This means that the flexible body may be inserted into an opening having a diameter of approximately "D" up to the point where the collar engages the opening. At that point, the retaining collar engages the walls wherein the opening has been created and is retained therein.

Advantageously, the short thin configuration of the electrode array 60 allows the electrode array 60 to be inserted within the first section of the scala tympani with minimal trauma by simply penetrating the round window membrane that separates the inner ear from the middle ear. The collar 66 allows stable retention of the electrode 60 within the round window membrane with minimal effect to the normal function of the cochlea with respect to acoustic stimulation.

The insertion technique for the electrode array embodiment shown in FIG. 8 is illustrated in FIGS. 9 and. 10. As a first step (FIG. 9), a hole 82 having a diameter "D" is punched or drilled through the round window membrane 80. (The round window 80, also known medically as the fenestra rotunda, comprises the opening between the scala tympani 52 of the cochlea 50 and the middle ear.) Next, as a second step (FIG. 10), an insertion tool 70 holds a proximal end of the array 60, while the distal end of the array 60 is inserted through the hole 82 until the retaining collar 66 engages the perimeter of the hole 82. The retaining collar 66 thus retains the electrode in a stable position within the cochlea.

As described above, it is thus seen that the present invention provides an electrode array suitable for insertion into the cochlea having a drug delivery channel therein. Thus, with such electrode array, electrical stimuli may be applied near the modiolar wall of the cochlea, or elsewhere, via spaced-apart electrode contacts embedded within a flexible carrier. When inserted into the scala tympani, the electrode contacts may be held against the modiolar wall by a positioner placed on the back side of the flexible carrier. Drugs may then be delivered deep into the cochlea through the drug delivery channel that passes longitudinally through the center of the flexible carrier.

As described above, it is further seen that the invention provides a method of making an electrode array having a drug delivery channel.

It is also seen from the description above that the invention advantageously provides a mechanism for delivering drugs deep inside the scala tympani of a cochlea even when the scala tympani is already occupied with an electrode array.

While the invention herein disclosed has been described by means of specific embodiments and applications thereof, numerous modifications and variations could be made thereto by those skilled in the art without departing from the scope of the invention set forth in the claims.

What is claimed is:

1. An electrode system adapted for use with a tissue stimulation device comprising:
   an electrode array comprising an elongate flexible carrier, a plurality of spaced-apart electrode contacts exposed along at least one surface of the flexible carrier, and wires embedded within the flexible carrier and connected to the electrode contacts;
   a flexible positioner adapted for insertion into a body cavity, said flexible positioner having front and rear sides, said body cavity having front and back walls, said flexible positioner being adapted for insertion into the body cavity so that the positioner assumes a position within the body cavity having its rear side lie against the back wall of the cavity, and leaving an open channel between the front side of the positioner and the front wall of the body cavity;
   wherein the electrode array and the flexible positioner may both occupy the body cavity at the same time, with the electrode array being located within the open channel created between the front side of the positioner and the front wall of the body cavity so that the electrode contacts of the electrode array are positioned adjacent the front wall of the body cavity; and
   drug delivery means for delivering a drug into the body cavity while the body cavity is occupied by the flexible electrode array and the flexible positioner.

2. The electrode system as set forth in claim 1 wherein the body cavity comprises a cavity within a human cochlea, and wherein the flexible positioner comprises a curved flexible positioner having a groove running longitudinally along its front side.

3. The electrode system as set forth in claim 1 wherein the drug delivery means comprises a channel or duct passing longitudinally through the elongate flexible carrier of the flexible electrode array, whereby a drug may be continuously delivered through the channel or duct to a distal location within the body cavity.

4. The electrode system as set forth in claim 1 wherein the drug delivery means comprises a channel or duct passing longitudinally through the flexible positioner, whereby a drug may be continuously delivered through the channel or duct to a distal location within the body cavity.

5. An implantable flexible cochlear electrode array comprising:
   an elongate flexible carrier insertable into the scala tympani of a human cochlea;
   a multiplicity of electrode contacts exposed on a surface of the flexible carrier, wherein each electrode contact comprises a flat platinum electrode exposed only on a front surface of the flexible carrier, the front surface comprising that surface of the flexible carrier that is placed closest to a modiolar wall of the scala tympani when the electrode array is inserted into the scala tympani;
   a multiplicity of wires embedded within the flexible carrier, each wire having a distal end connected to a respective electrode contact and a proximal end connectable to a tissue stimulation device; and
   a drug delivery channel passing longitudinally through the flexible carrier.

6. The implantable flexible cochlear electrode array as set forth in claim 5 further comprising a multiplicity of electrode contacts exposed on the surface of the flexible carrier.

7. The implantable flexible cochlear electrode array as set forth in claim 6 wherein each electrode contact comprises a platinum ring electrode that encircles the flexible carrier.

8. The implantable flexible cochlear electrode array as set forth in claim 6 wherein each electrode contact comprises a flat platinum electrode exposed only on a front surface of the flexible carrier, the front surface comprising that surface of the flexible carrier that is placed closest to a modiolar wall of the scala tympani when the electrode array is inserted into the scala tympani.

9. The implantable flexible cochlear electrode array as set forth in claim 5 further including a retention collar formed proximally on the flexible carrier so that the multiplicity of electrode contacts lie distally therefrom, the retention collar having a shoulder adapted to engage an opening created in the round window membrane at the entrance of the scala tympani, whereby the retention shoulder anchors the electrode array within the scala tympani.

10. The implantable flexible cochlear electrode array as set forth in claim 9 wherein the flexible carrier extends distally from the shoulder a distance of between about 3 mm to 6 mm.

11. An elongate flexible positioner for insertion into a body cavity having front and back walls, said flexible positioner having front and rear sides, said elongate flexible positioner being insertable into the body cavity so that the positioner assumes a position within the body cavity having its rear side lie against the back wall of the cavity, and leaving an open channel between the front side of the positioner and the front wall of the body cavity, said elongate flexible positioner further having a drug delivery channel passing longitudinally therethrough.

12. A method of making an implantable electrode array having a drug delivery channel passing therethrough, the method comprising:

(a) attaching electrode contacts made from a precious, biocompatible material to a foil sheet made from a non-toxic but chemically-active metal;

(b) connecting a wiring system to the metal contacts;

(c) positioning a flexible tube over the wiring system, the flexible tube having a lumen passing therethrough;

(d) molding a flexible polymer carrier around the electrode contacts, wiring system and flexible tube while such are held in place by the foil sheet; and (e) etching away the foil sheet, leaving the electrode contacts exposed at a surface of the molded polymer carrier; whereby a flexible implantable electrode array is made, and wherein the lumen of the flexible tube comprises a channel through which drugs or other liquids may be delivered to a distal tip of the electrode array.

13. The method of claim 12 wherein step (d) comprises molding the flexible polymer carrier so that the resulting electrode array assumes a naturally curved shape.

14. The method of claim 12 wherein step (d) comprises molding the flexible polymer carrier so that the resulting electrode array assumes a naturally straight shape.

15. The method of claim 12 wherein step (c) comprises positioning a flexible silastic tube over the wiring system and temporarily plugging its lumen at its distal end while carrying out step (d), thereby preventing the flexible polymer mold from flowing into the lumen of the silastic tube during the molding process.

16. The method of claim 12 wherein step (a) comprises forming each electrode contact from first and second metallic strips, attaching a central portion of the first strip to the foil sheet and laying the second strip over the first and attaching a central portion of the second strip to the first strip, and wherein step (b) comprises folding at least one portion of the first strip back over second strip and at least one wire, and electrically bonding the at least one wire to the folded over strip.

17. A method of inserting a short cochlear electrode array through the round window membrane into the scala tympani of a human cochlea, the cochlear electrode array comprising an elongate flexible carrier having a retention collar having an engaging diameter "D" thereon, at least one electrode contact exposed on a surface of the carrier and located distally from the retention collar, at least one wire embedded within the flexible carrier having a distal end connected to the at least one electrode contact and a proximal end connectable to a tissue stimulation device, the method comprising the steps of:

(a) forming a hole having a diameter "D" in the round window membrane;

(b) attaching a proximal end of the short cochlear electrode array to an insertion tool;

(c) inserting a distal end of the short cochlear electrode array through the opening in the round window membrane until the retention collar engages the round window membrane; and (d) removing the insertion tool from the proximal end of the short cochlear electrode array.

18. An implantable flexible cochlear electrode array comprising:

an elongate flexible carrier insertable into the scala tympani of a human cochlea;

at least one electrode contact exposed on a surface of the flexible carrier;

at least one wire embedded within the flexible carrier, said at least one wire having a distal end connected to the at least one electrode contact and a proximal end connectable to a tissue stimulation device;

a drug delivery channel passing longitudinally through the flexible carrier; and a retention collar formed proximally on the flexible carrier so that the at least one electrode contact lies distally therefrom, the retention collar having a shoulder adapted to engage an opening created in the round window membrane at the entrance of the scala tympani, whereby the retention shoulder anchors the electrode array within the scala tympani.

19. The implantable flexible cochlear electrode array as set forth in claim 18 further comprising a multiplicity of electrode contacts exposed on the surface of the flexible carrier.

20. The implantable flexible cochlear electrode array as set forth in claim 18 wherein the at least one electrode contact comprises a platinum ring electrode that encircles the flexible carrier.

21. The implantable flexible cochlear electrode array as set forth in claim 18 wherein the at least one electrode contact comprises a flat platinum electrode exposed only on a front surface of the flexible carrier, the front surface comprising that surface of the flexible carrier that is placed closest to a modiolar wall of the scala tympani when the electrode array is inserted into the scala tympani.

22. The implantable flexible cochlear electrode array as set forth in claim 18 wherein the flexible carrier extends distally from the shoulder a distance of between about 3 mm to 6 mm.

* * * * *

UNITED STATES PATENT AND TRADEMARK OFFICE
CERTIFICATE OF CORRECTION

PATENT NO. : 6,309,410 B1
DATED : October 30, 2001
INVENTOR(S) : Kuzma et al.

It is certified that error appears in the above-identified patent and that said Letters Patent is hereby corrected as shown below:

<u>Title page,</u>
Item [75], change the named inventors from "Janusz A. Kuzma, Englewood, Co (US); Thomas H. R. Lenarz; Rolf-Dieter Battmer, both of Hannover (DE); Alfred E. Mann, Hollywood, CA (US)" to -- Janusz A. Kuzma, Englewood, Co (US); Thomas H. R. Lenarz; Rolf-Dieter Battmer, both of Hannover (DE); Thomas J. Balkany, Coral Gables, FL (US); Alfred E. Mann, Hollywood, CA (US) --

Signed and Sealed this

Eighteenth Day of March, 2003

JAMES E. ROGAN
*Director of the United States Patent and Trademark Office*